United States Patent [19]

Fuchs

[11] 4,130,800
[45] Dec. 19, 1978

[54] MAGNETIC PARTICLE TEST SYSTEM USING MOVABLE TEST PIECE CLAMPING MEANS MOVABLE JOINTLY OR INDEPENDENTLY

[75] Inventor: Ernst E. Fuchs, Schmerikon, Switzerland

[73] Assignee: Mecafina S.A., Schmerikon, Switzerland

[21] Appl. No.: 827,607

[22] Filed: Aug. 25, 1977

[30] Foreign Application Priority Data

Aug. 31, 1976 [CH] Switzerland .................. 11022/76

[51] Int. Cl.² .................................. G01R 33/12
[52] U.S. Cl. ........................................ 324/216
[58] Field of Search .......................... 324/214–216, 324/263; 361/143–145

[56] References Cited

U.S. PATENT DOCUMENTS

| | | | |
|---|---|---|---|
| 3,614,604 | 10/1971 | Reinshagen | 324/216 |
| 3,784,904 | 1/1974 | Suzuki et al. | 324/215 |

FOREIGN PATENT DOCUMENTS

| | | | |
|---|---|---|---|
| 2113084 | 10/1971 | Fed. Rep. of Germany | 324/216 |
| 340956 | 6/1972 | U.S.S.R. | 324/263 |

Primary Examiner—Robert J. Corcoran

[57] ABSTRACT

The present invention relates to an installation for showing up faulty areas on the surface of a bar-shaped, magnetizable workpiece. The installation comprises a feed station and delivery station for the workpiece, and a treatment station, arranged between the feed station and the delivery station, for the introduction onto and fixing of a ferromagnetic powder on the workpiece. The installation includes a support having guide rails between and through the station, clamping devices displaceable along the support and for clamping the workpiece and connecting it to an electrical circuit each clamping device having a drive device with a drive cable. The drive devices are connected with each other by means of a clutch coupling; and, the installation has a control device for regulating operation of the whole installation.

12 Claims, 25 Drawing Figures

MAGNETIC PARTICLE TEST SYSTEM USING MOVABLE TEST PIECE CLAMPING MEANS MOVABLE JOINTLY OR INDEPENDENTLY

The invention relates to an installation for showing up faulty areas on the surface of a bar-shaped magnetizable workpiece.

Processes and installations for showing up faulty areas on the surface of bar-shaped, magnetizable workpieces are already known, but these have considerable inherent disadvantages.

For example, it is known to pass current through the workpiece and to make stray fields, in the lines of force, which are produced by faulty areas on the surface of the workpiece visible by spraying on a ferro-magnetic powder. The accumulations of powder which show up the faulty areas are covered with a colouring layer, so that after de-magnetization of the workpiece the accumulations of powder either fall off unaided or are carried away by a current of air, so that the faulty area is recognisable as a region which is not covered by the colouring.

This process has the disadvantage of requiring a large amount of colouring material added to which it is necessary to use a quick drying colouring, which easily leads to a blocking up of jets and conduits. Also, the introduction of the liquid lacquer limits the field of application and the efficiency of such an installation, since drying of the lacquer requires a certain amount of time.

It has already been suggested in order to improve the process, to make up a composition of the particles of the powder consisting of iron, pigment and lacquer and to introduce this in solid form onto the surface of the workpiece and to spray the accumulations of powder which form with a solvent, whereupon the particles of the powder can be caused to adhere to each other and onto the surface of the workpiece due to an at least partial softening of the lacquer.

The installations which have been used up until now for carrying out such a process have considerable shortcomings and have shown themselves to not be utilizable. For example, rails, on which clamping devices for clamping the workpiece are displaceable, tend to become heavily soiled and cannot be cleaned. Chain drives which drive the clamping devices become contaminated with powder very quickly, which leads to jamming, irregular drive and heavy wear of the chain drive. Also the control of the installation, in the known case, takes place by means of cables which are dragged along together with the accomodating devices, and these can also give rise to faulty operation. The clamping devices which can be displaced in opposite directions clamp the workpiece by means of spring devices and clamping jaws which are not only bulky and expensive but which also give rise to considerable faults in operation.

It is the object of the invention, to provide an installation for showing up faulty areas on the surface of a bar-shaped, magnetizable workpiece, which is exact, efficient and reliable in operation.

The installation for showing up faulty areas on the surface of a bar-shaped magnetizable workpiece according to the invention includes:
(a) a feed station;
(b) a delivery station for said workpiece:
(c) a treatment station, arranged between said feed station and said delivery station, for the introduction onto and fixing of a ferromagnetic powder on said workpiece;
(d) a support having guide rails between and through said stations;
(e) clamping devices displaceable along said support and for clamping said workpiece and connecting it to an electrical circuit;
(f) a drive device, having a drive cable, associated with each clamping device, said drive devices being connected with each other by means of a clutch coupling; and,
(g) a control device for regulating operation of said installation.

Embodiments of an installation according to the invention will now be described in more detail with reference to the schematic drawings, there being shown in.

Figure 1:
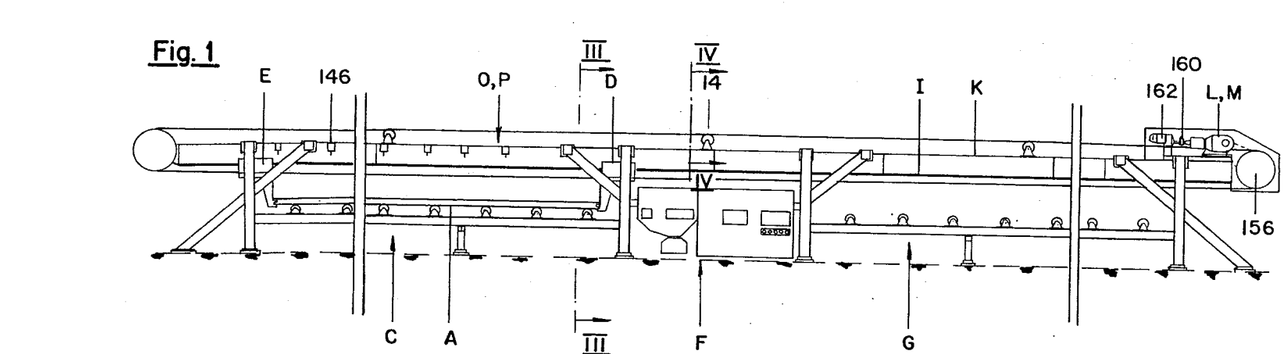
FIG. 1 a installation for showing up faulty areas on the surface of bar-shaped magnetizable workpieces seen from the side.
Figure 2:
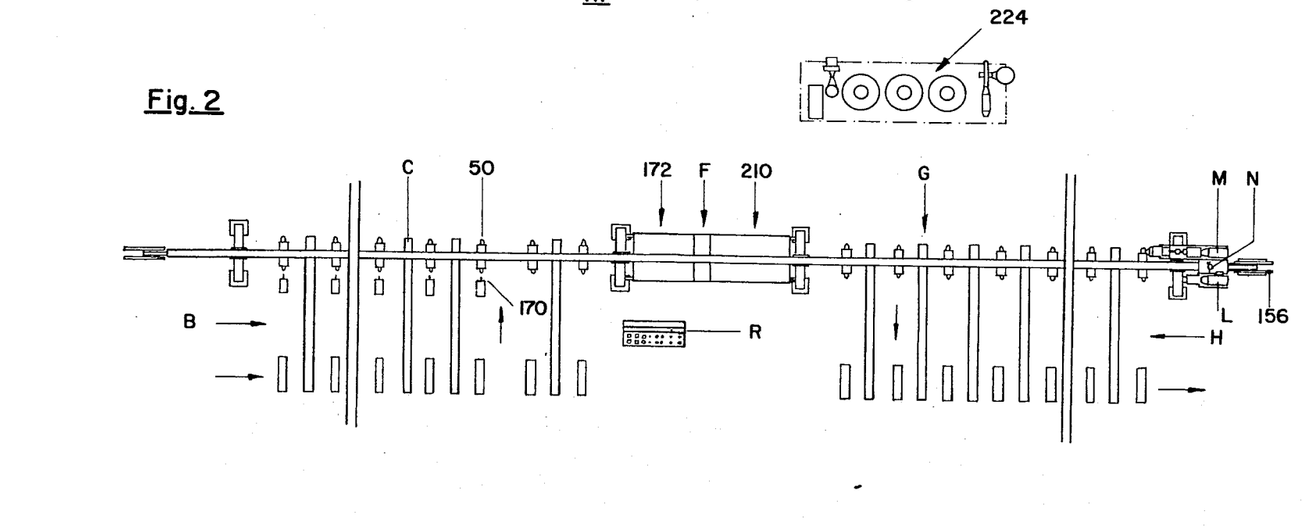
FIG. 2 the installation according to FIG. 1 in outline.
Figure 3:
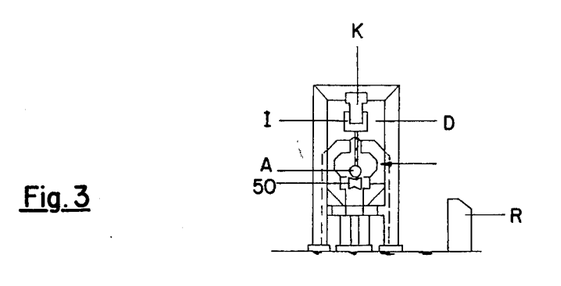
FIG. 3 the installation in section III—III of FIG. 1.

FIGS. 1–3 show the basic construction of an installation for showing up faulty areas on the surface of bar-shaped, magnetizable workpieces A, such as for example billets of steel. The workpieces arrive at a feed station C via a feeding unit B. Here an individual workpiece A is grasped by clamping devices D and E, connected to a current circuit, in order to produce an electromagnetic field around the surface of workpiece A and conveyed through a treatment station F in which workpiece is treated by means of a ferromagnetic powder, to a delivery station G. After the workpiece has been released from the clamping devices, it is transported away by means of a carrying-off device H. The clamping devices D and E are guided along rails I, which are arranged on a support K. Each clamping device D and E has its own drive device L and M respectively, these being connectable together via a clutch coupling N and each having a drive cable O,P for operating the clamping devices D and E. The clamping devices D,E have, contact pieces in connection with conductor rails as will be described in detail, for connecting the workpieces to the current circuit. A control device R has the purpose of controlling the installation.

Figure 4:
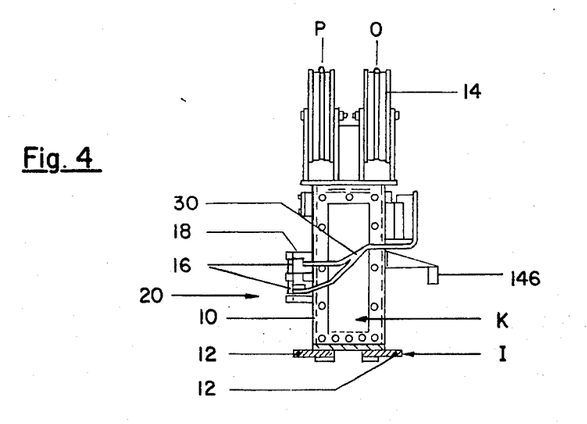
FIG. 4 the support with rails and current rails in section IV—IV of FIG. 1 and on a larger scale.

The support K, as is particularly apparent in FIG. 4, consists of a hollow elongated body 10 having rectangular cross-section, on whose underside the running rails I are arranged as flanges 12 which project at the sides. The exposed running rails I are easily cleaned by wipers in the clamping devices. The support K moreover has guide rollers 14 for the drive cables O and P. Drive cable O has two ends which both are connected to the carriage 32 of clamping device D. From the carriage 32 the cable O extends leftwards as shown in FIG. 1, to a return pulley at the left-hand end of the support K, and then passes over the guide rollers 14 to another return pulley at the right-hand end of the support K, and thereafter returns to the carriage 32. The last mentioned pulley is connected to the drive device L. The other drive cable P extends parallel to the cable O, but is connected to the carriage of the clamping device E and runs over a return pulley which is coupled to the drive device M. Thus, each drive cable O,P forms a closed loop which is drivable by one or the other of the drive devices L and M. Conductor rails 16 are arranged, spaced apart, on the side of the support with an intermediate layer of electrical insulation 18. This insulation preferably consists of wood and has the particular purpose, of reducing the passage of magnetic flux to the support, in order in this way to keep electrical losses at a low value.

Figure 5:
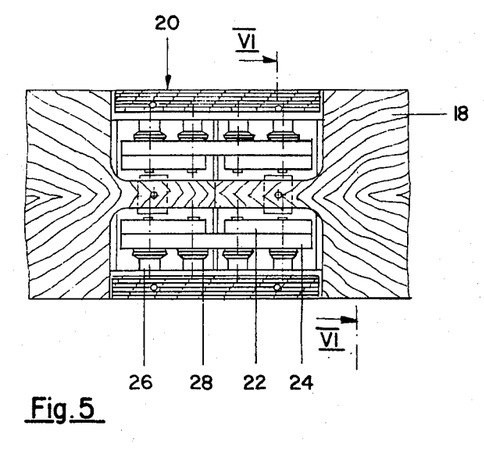
FIG. 5 the connecting device of sections of the current rails in section IV—IV of FIG. 6.
Figure 6:
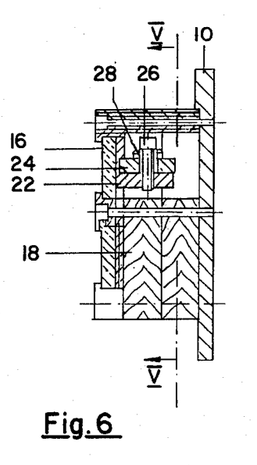
FIG. 6 the connecting device for the current rails of FIG. 5 in section VI—VI of FIG. 5.

At areas 20 of the conductor rail 16, either for introducing the current or for joining individual sections of the rail, as can be seen in FIGS. 5 and 6, the rail 16 is provided with lateral projections 22, against which connecting members 24 are pressed by means of threaded bolts 26 and spring members 28. The connecting members 24 can either form the connection to a further length of conductor rail or be connected with a current supply cable 30. Current is supplied preferably from a position between the feed station C and the delivery station G, ie, practically in the middle region of the treatment station S, in order to maintain over the whole path of travel of the clamping devices D,E, and in particular along the treatment station F an electrical resistance which is as uniform as possible and in this way to keep the magnetization around the workpiece as constant as possible when the latter moves along the operating path and in particular along the treatment station.

Figure 7:
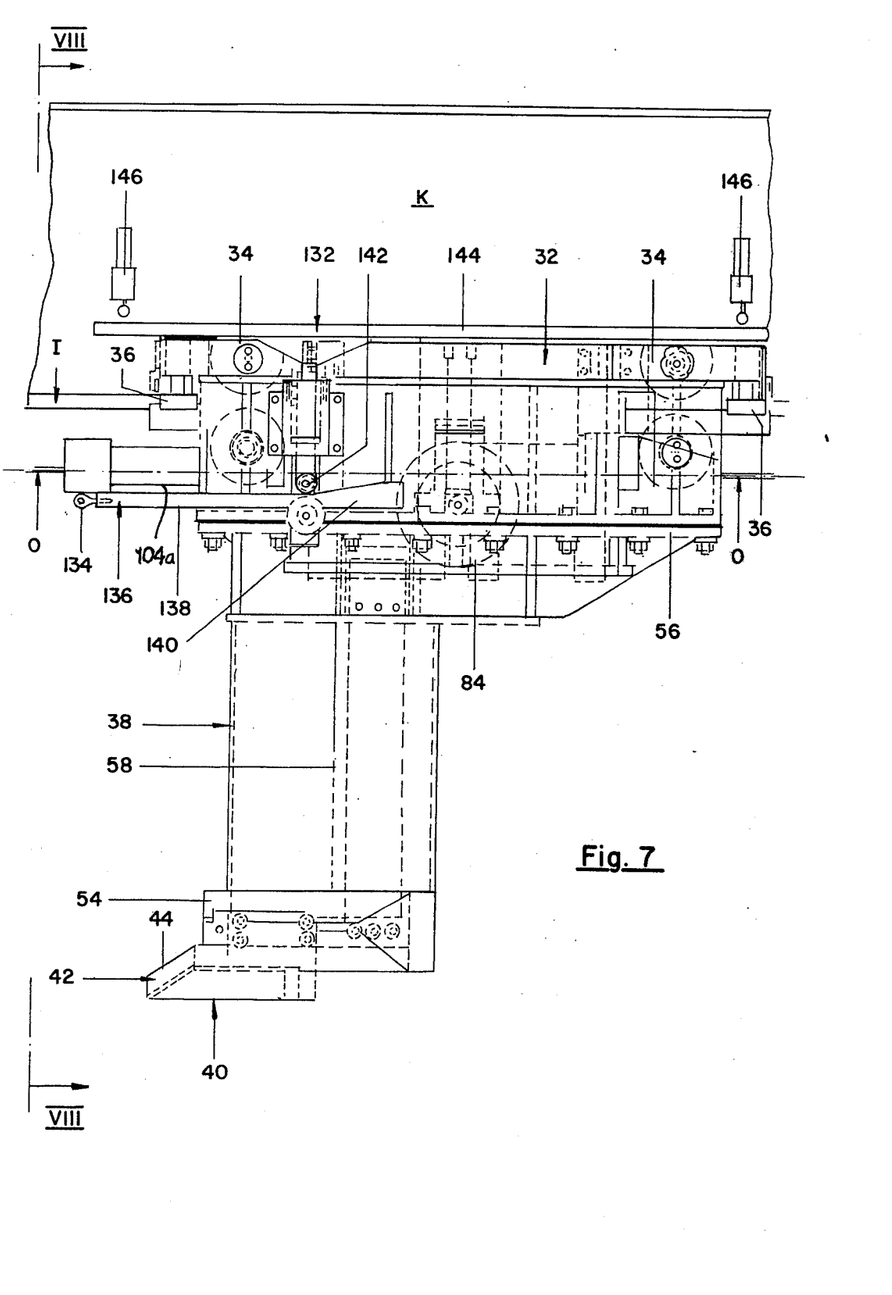
FIG. 7 the clamping device for the workpiece which is displaceable on the rails, with a clamping device and a monitoring device for clamping, in side view.
Figures 8, 9:
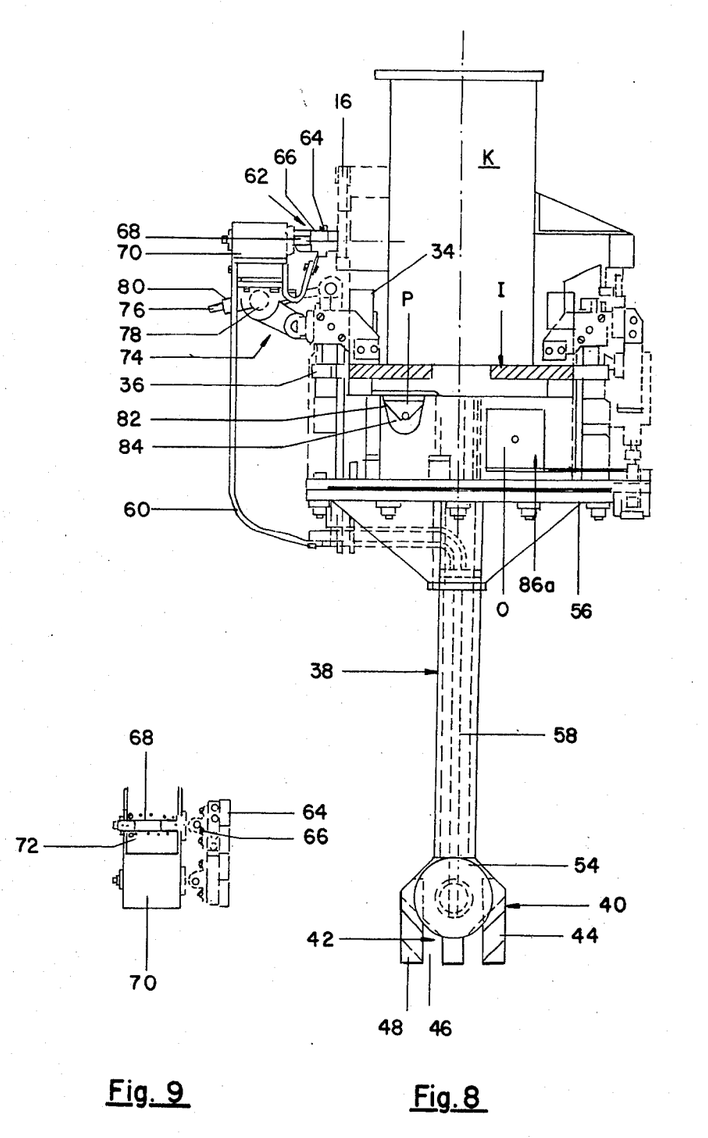
FIG. 8 the clamping device of FIG. 7 in section VIII—VIII of FIG. 7.
FIG. 9 the current take-off of the clamping device as a separate part in plan view, partly in section.

The clamping devices D,E have practically identical constructions, the clamping device D which, in the direction of feed, is at the front end having only in addition a tension device and a monitoring device, which will be described in more detail below. As shown in FIGS. 7 and 8 each clamping device has a carriage 32, with four pairs of running rollers 34, which engage with the upper and lower sides of the guiding rails I. To provide side guiding, four guiding rollers 36 which engage with the edge of the rails are provided, their axis being vertical. At least a portion of the running rollers 34 and/or the guiding rollers 36 have an eccentric bearing arrangement, so that they are adjustable with regard to their distance in relationship to the guiding rails. The eccentric bearing arrangement and the adjusting facilities are not shown in detail.

The clamping devices D,E each have an arm 38 arranged on the carriage 32, which arms have on their lower end opposing workpiece holders 40. The latter have in section triangular accomodating hollows 42 with oblique abutment surfaces 44, in order to facilitate gripping of the workpieces. The workpiece holders are furthermore divided by means of grooves 46 into individual holding fingers 48, for passing through grooves 53, which are arranged in stationary supporting surfaces 51 or rolling supporting surfaces 52 of the support members 50 (see FIG. 16), in order to engage with the underside of the workpiece and to facilitate its accomodation. The arms 38 have moreover, in the region of the accomodating hollows 42, electrical contact pieces 54 by means of which the workpieces can be connected into the current circuit to provide the magnetic field. The arm 38 is electrically separated from the carriage 32 by means of an insulating layer 56. A conductor 58 which is arranged in the arm 38 has the purpose of supplying current to the contact piece 54. The conductor is connected via one or more cables 60 to a current collector 62, which is arranged on the carriage 32.

The current collector 62 comprises several contact blocks 64, for example carbon block, which are arranged on rockers 66, which is particularly apparent in FIG. 9. The rockers are supported on elongate holders 68 so that they may tilt, the holders in their turn being axially displaceable in a support frame 70. The holders 68 and hence the contact blocks 64 are biased in the direction of the current rails 16 by means toward springs 72. The support frame 70 is arranged so that it may be tilted and can be fixed in its position by means of an adjusting device 74. For this purpose the carriage 32 has a spindle 76 which can be tilted, which is guided by a lug 78 which can be tilted in the support frame 70. An adjusting bolt 80 makes it possible to adjust the position of the support frame 70 relative to the current rail 16. With the aid of the adjusting device 74 the position of the contact block 64 relative to the current rails 16 can be adjusted as well as the pressing force which is provided by the springs 72.

Drive of each clamping device D,E is provided by drive devices L,M and corresponding drive cables O,P. Regarding the clamping device D shown in FIG. 8 the drive cable P, which serves the purpose of driving the other clamping device E, is guided through a cut-out portion 82 and on a guiding roller 84 which is provided on the carriage.

Figure 10:
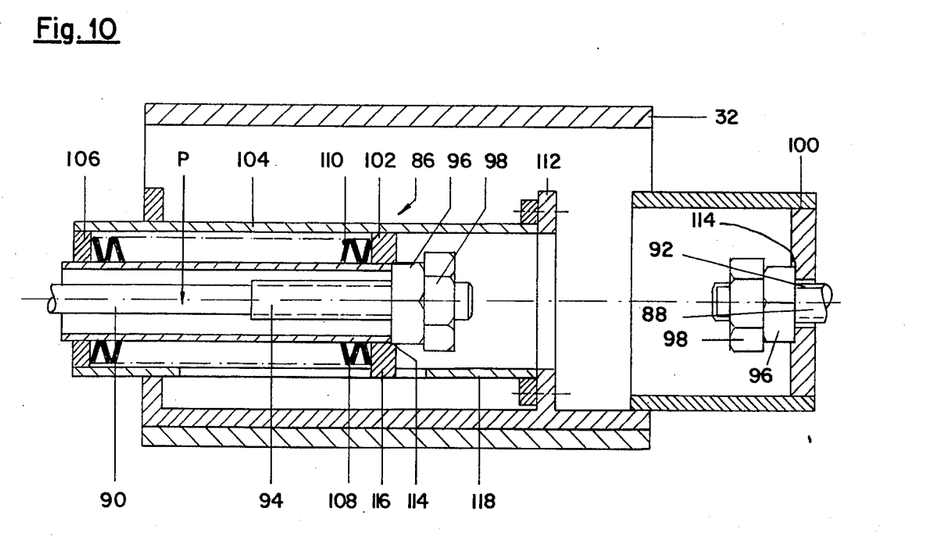
FIG. 10 the clamping device of the clamping device for the drive cable, on an enlarged scale and in longitudinal section.

Drive cable P is connected to the carriage 32 of the clamping device E via a tension device 86 as shown schematically in FIG. 10. For this purpose the two ends 88 and 90 of the cable are fastened to or sleeves threaded rods 92 and 94, which carry clamping nuts 96 and check nuts 98. Whereas one cable end 88 is connected to an abutment 100 which is arranged fixedly on the carriage 32, the threaded rod or sleeve 94 at the other cable end 90 is supported on a piston 102, which is guided in a cylindrical housing 104. Between the piston 102 and an end plate 106 of the cylindrical housing 104 a spring device 108 consisting of a packet of individual cup springs 110 is arranged.

The other end of cylindrical housing 104 is fastened to an abutment 112 of the carriage 32. Means to prevent twisting of the cable and thus unwinding of the cable P during operation are provided by the abutment 100 and the piston 102 having countersunk grooves 114, against which the clamping nuts 96 lie, the clamping nuts 96 having two parallel surfaces lying in the grooves. The check nuts 98 prevent the clamping nuts 96 from coming loose. Furthermore, the piston 102 is provided with a projection 116, which engages with a longitudinal slit 118 of the cylindrical housing. The tension in traction cable P can be adjusted by screwing up the clamping nuts 96 to a greater or lesser extent and hence compressing the spring device 108. In order to make possible adjustment of the right-hand clamping nut 96, screwed on threaded rod or sleeve 92 a device (which is not shown) is used, to pull the right-hand portion of the cable P toward the carriage 32 whereby the opposite end 90 of the cable is correspondingly moved leftwards and the spring device 108 is compressed. The cable is thus displaced with respect to the carriage 32 so that makes possible pretensioning of the cable and a raising out of the right-hand clamping nut 96 is raised out of the groove 114 in the abutment 100 and can be turned thereafter.

Figure 11:
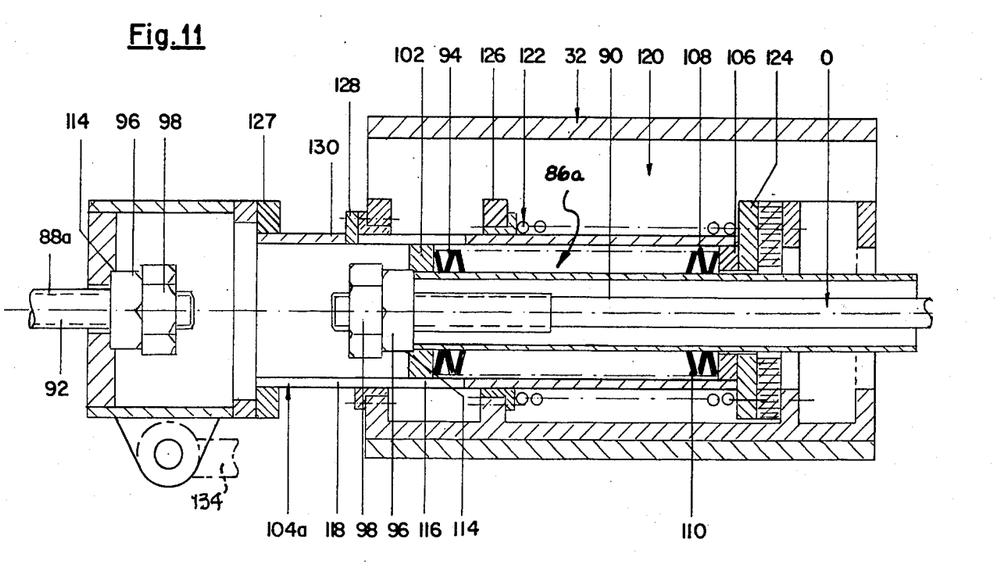
FIG. 11 the bracing device for bracing the clamping devices with respect to each other with a workpiece in position on an enlarged scale and in longitudinal section.

The clamping device which is shown in FIG. 8 has additionally to the tension device 86a a supplementary tension device 120, in order to urge the clamping devices D,E when the workpiece A is in position together by means of the drive cables O,P and to hold the workpiece firmly in position. Such supplementary tension device 120 as shown in FIG. 11, also has a spring device 122, by means of which one end 88a of the drive cable O is connected to the carriage 32 of clamping device D.

In the embodiment shown the spring device 122 consists of a compression spring, which surrounds a cylinder 104a containing the clamping device 86a and which is interposed between an end plate end 124 of cylinder 104a and an abutment 126 of the carriage 32, the cylinder in this case being displaceable in chassis 32. In this case the cable end 88a is not fastened to the carriage 32, but rather to a member 127 fixed to that end of the cylinder 104a which is remote from the cylinder base 106. The cylinder 104a which is displaceable in the carriage 32 is also provided with means for preventing rotation, this being provided by a projection 128 which engages with a slit 130 of the cylinder. The supplementary tension device 120 allows the drive cable O which is tensioned by means of the tension device 86a to be displaced with respect to the carriage 32 whereby the spring device 122 is compressed, which will be explained in more detail below. The amount of extension of cylinder 104 out of the carriage 32 gives an indication of the loading of the spring device 122. By suitable calibration of the length of extension the spring loading can be read off directly, particularly so when the cylinder 104 projects out of the carriage, as is shown in FIG. 7.

The installation has a monitoring device 132, which serves the purpose of monitoring the clamping of the clamping devices D,E with respect to each other with the workpiece A in place. This monitoring device 132 is preferably arranged on the clamping device D, which contains the supplementary tension device 120. The cylinder 104a is connected via a coupling member 134 to a control bar 136 which is arranged to extend parallel to the support K at the side of carriage 32. It has a first cam part 138 for use in indicating inadequate and a second cam part 140 for use in indicating adequate loading of the spring device 122. The bar 136 which is displaceable with respect to the carriage 32 proportionally to the displacement of cylinder 104a co-operates with a cam follower member 142 which is also carried displacably in the carriage 32 the member carrying an actuating rail 144 which is arranged parallel to the support K. The rail co-operates with electric control switches 146, which are arranged along the support K and whose spacing is smaller than the length of the actuating rail 144 so that upon lifting the cam follower 142 by means of the control bar 136, the actuating bar enters into engagement with at least one of the switches 146 independently of the actual position of the clamping device D along the support K. The switches 146 are connected to the control device R. If the tension forces exerted by the clamping devices D,E on a workpiece is small, then the cylinder 104a only projects for a small distance out of the carriage 32 and the cam follower member 142 is located on the first cam part 138 for inadequate tensioning. Corresponding to this the switches 146 are also brought to a position which shows that the bracing between the clamping devices is inadequate. The amount of bracing of the clamping devices must then be increased, until the cam follower member 142 arrives on the second cam part 140, which signals that adequate bracing of the clamping devices is present. The actuating rail 144 then actuates at least one of switches 146 and hence a signal is transmitted to the control device R. The monitoring device does not only operate during the bracing of the clamping devices, but also carries out monitoring during the movement of the clamping devices from the feed station to the delivery station of the degree of bracing which is necessary for holding the workpiece A.

Figure 12:
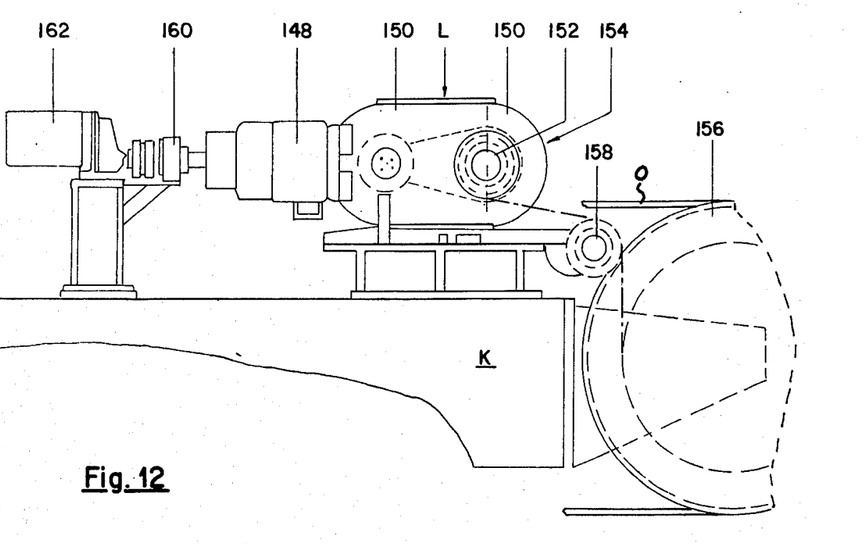
FIG. 12 the drive device with auxiliary drive for the drive cables of the clamping devices, in side view.
Figure 13:
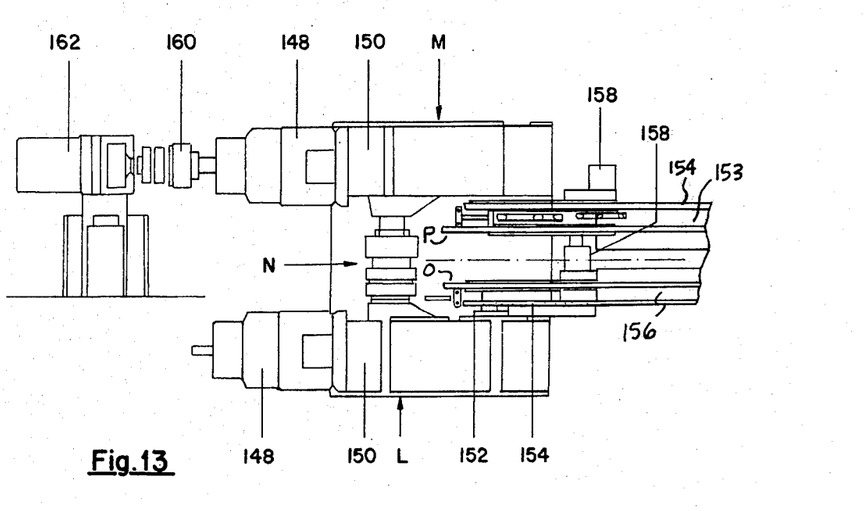
FIG. 13 the drive devices of FIG. 12, in outline.

FIGS. 12 and 13 show details of the drive devices L,M for the clamping devices D,E. Each drive device has a motor 148 with gear units 150. The gear units 150 of the drive devices L,M are connectable together via the clutch coupling N. Each gearing has a chain wheel 152 on which a chain 154 produces the connection to the drive or return pulley 156 for the drive cable O or P. Each drive device L,M further has a monitoring device for the direction of rotation 158 which is connected to the control device R. The monitoring devices have the purpose of monitoring the direction of rotation of the drive devices. Particularly when the drive devices L,M are being braked by means of a current in the opposite sense the monitoring devices for the direction of rotation show when the drive devices begin to run in the opposite direction, so that the opposing current for braking can be switched off at the correct moment.

One of the drive devices M is connectable to an auxiliary drive device 162 via an auxiliary clutch coupling 160 which, when the clutch coupling N is out of engagement and the auxiliary clutch coupling 160 is in engagement, allows the drive cable P to be moved relative to the drive cable O, in order to brace the clamping devices D,E, by means of the supplementary tension device 120, this being with a speed which is reduced with respect to that of the drive devices L,M for joint movement of the clamping devices D,E, from the feed to the delivery station. The drive devices L,M are moreover so constructed that they carry out the return movement of the clamping devices D,E from the delivery to the feed at a greater speed than the speed of the advancing stroke. Control of the drive devices and the auxiliary drive device together with the clutch coupling and the auxiliary clutch control take place via the coupling device R.

Figure 14:
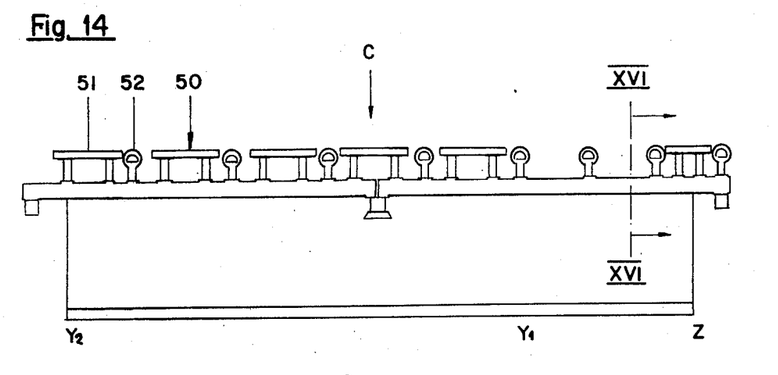
FIG. 14 the arrangement of supporting members of the feed station in side view.
Figure 15:
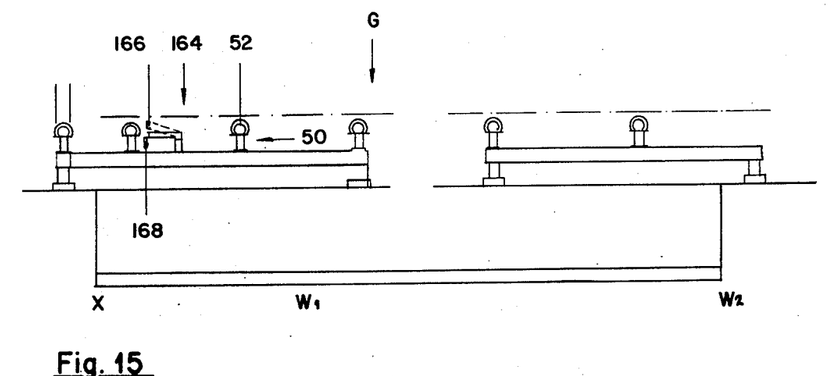
FIG. 15 the arrangement of supporting members of the delivery station in side view.
Figure 16:
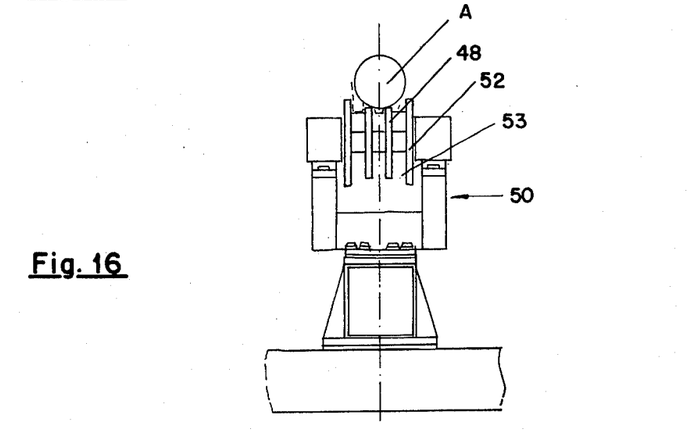
FIG. 16 a supporting member with rolling bearing surfaces according to the line XVI—XVL of FIG. 14.

The parts of the feed station C and the delivery station G are shown in FIGS. 14–16. As can be seen from FIG. 14, the feed station has supporting members 50 with stationary supporting surfaces 51 or rolling supporting surfaces 52, which in each case have grooves 53 for the holding fingers 48 of the workpiece holder 40 of the clamping devices D,E to pass through. In the feed station C, supporting members 50 with stationary supporting surfaces 51 and rolling supporting surfaces 52 are in practice arrange alternately. In the delivery station G on the other hand only supporting members 50 with rolling supporting surfaces 52 are provided. The delivery station G moreover has a braking device 164, which has a brake lining 166 and a raising device 168, for pressing the brake lining 166 against the workpiece A which has been forwarded to it. In this way the removal of the workpiece from the clamping device is made easier and jamming is avoided. The braking device is so arranged, that is is in each case nearer to the halting position of the rear clamping device E in the delivery station.

The installation is preferably so constructed, that in the feed station the starting position Z of the forward clamping device D is fixed and the starting position of the rear clamping device E can vary between positions $Y_1$ and $Y_2$. In the delivery station G on the other hand the stopping position X of the rear clamping device E is fixed and the stopping position of the forward clamping device D is variable. The fixed starting position Z in the feed station C and the fixed stopping position X in the delivery station G lie close to the treatment station S. In this way the shortest lengths of displacement are obtained and workpieces for example having a length of 4 to 13 meters can be treated. The fixed starting position Z of the forward clamping device D in the feed station C and the fixed stopping position X of the rear clamping device E in the delivery station G can easily be determined by terminal switches. The variable stopping positions $W_1$ to $W_2$ of the forward clamping device D in the delivery station G is produced by the clamped workpiece A itself.

In order to avoid unnecessary displacement of the rear clamping device E in the feed station C and to bring the former to a halt immediately after the rear end of the workpiece to be treated, the workpiece A is first of all so arranged in the feed unit B, that its front end comes to lie at the fixed starting position C of the forward clamping device D. In the immediate proximity of the supporting members in the feed station C there are, as can be seen in FIG. 1, in the waiting position of the workpiece A, a row of sensor switches 170, which are operated by a waiting workpiece. The control device R is then programmed in such a way, that the drive device L of the rear clamping device E is then always switched off, when the first sensor switch 170 which is no longer operated, is reached.

Figure 17:
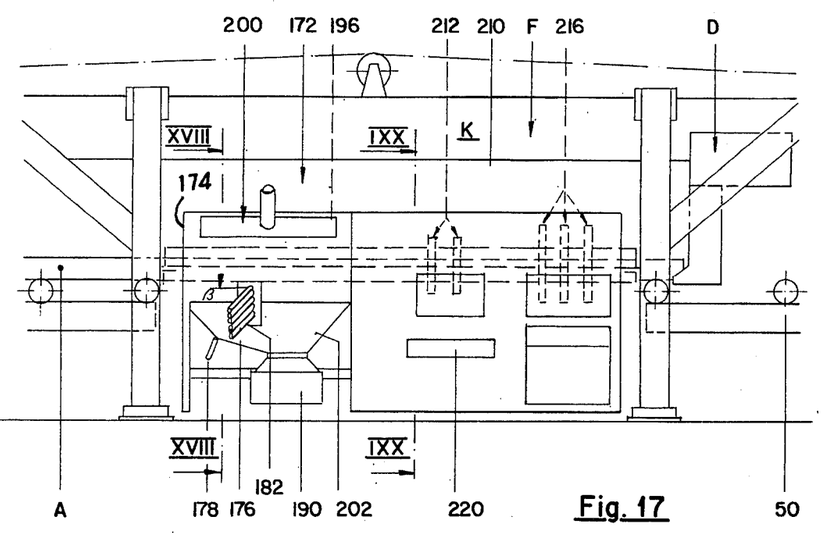
FIG. 17 the treatment station of the installation in side view.
Figure 18:
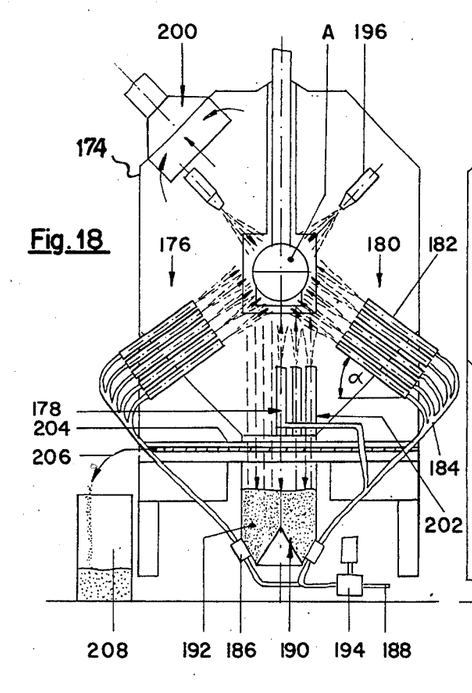
FIG. 18 the spraying device of the treatment station along line XVIII—XVIII of FIG. 17.
Figure 19:
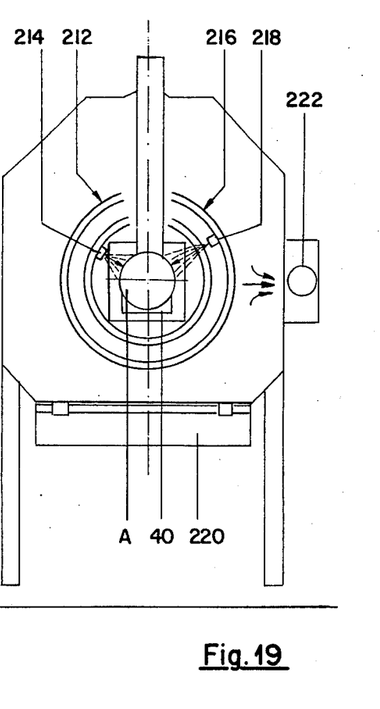
FIG. 19 the fixing device of the treatment station along the line IXX—IXX of FIG. 17.

FIGS. 17 to 19 show details of the treatment station F. First of all the treatment station has a spraying device 172, which contains a spray chamber 174, for spraying the powder on and taking up excess powder. This spraying device has a number of sets of spraying jets 176, 178 and 180 which are arranged around the treatment region of the workpiece A. Two side sets of spraying jets 176 and 180 are inclined at an angle $\alpha$ of for example 50°–60° to the horizontal. The set of spraying jets are furthermore inclined preferably in the direction of travel of the workpiece at an angle $\beta$ (FIG. 17), which is so inclined as a function of the speed of travel of the powder, that the powder when it meets the workpiece has a velocity component, which corresponds to the speed of the workpiece. Angle $\beta$ can for example be 85° to the direction of travel. The sets of spray jets 176, 178 and 180 have individual spraying jets elements 182, which can be individually switched on, depending on the cross-sectional shape and size of the workpiece which is to be treated.

The individual spraying jet elements 182 are in each case connected by means of a conduit 184 with injectors 186, which are supplied with compressed air via compressed air conduits 188 and carry the powder 192 out of a storage container 190. The compressed air conduits 188 are connected to a source of compressed air which is not shown and include shut-off valves 194, which can be operated by the control device R depending on the dimensions of the workpiece which is to be treated. The spraying jet elements 182 of the spraying jet sets 176, 178, and 180 spray the workpiece A, which is to be treated with an excess amount of powder 192, so that at faulty areas of the workpiece, at which the electromagnetic line of force in the workpiece A through which the current has been passed are interrupted, the powder 192 is retained. The air blast jets 196 which follow the sets of spraying jets 176, 178 and 180 direct a current of compressed air 198 into the sprayed workpiece, in order to blow any excess powder Preferably the compressed air device for the set of spraying jets and the air blast jets is adjustable, in order to adjust the spraying and the air blasting to the composition of the powder and the speed of travel of the workpiece.

The spraying chamber 174 furthermore has a suction device 200 associated with it, whose suction performance is adjusted such that a depression with respect to atmosphereic pressure is created in the spraying chamber. In this way the occurrence of a mist of powder in the surroundings is prevented and dust-like components of the powder can be drawn off.

The spraying device also has a catching device 202 for excess powder with a sieve device 204 for separating out impurities 206, which are led to a collecting container 208. The sieve device 204 preferably takes the form of a swing sieve. The powder which has been collected passes to the storage container 190.

Following the spraying device 172 a fixing device 210 is provided, which in the present example has a device 212 for spraying on a fixing medium. The fixing medium is for example a non-explosive solvent such as methylene chloride, and serves the purpose of partially dissolving the powder. The spraying device 212 carries one or more nozzle scrolls 214, which apply the fixing medium to the workpiece A which has been treated with powder. As a variation to the example shown the fixing device can also for example be constructed as an inductive heating device.

The fixing device furthermore has a drying device 216, in order to dry the dissolved powder. In the present example this takes place by driving off the solvent. The drying device 216 contains one or more nozzle scrolls 218, which preferably blow warm air onto the treated workpiece. A catching device 220 collects powder which falls off and fixing medium which drips off. Furthermore, the fixing device is equipped with a suction device 222, for sucking off excess fixing medium and feeding it to a regenerating plant 224 (see FIG. 2). The regenerating plant is for example a known active carbon plant for reclaiming organic solvents.

The present treatment station is of particular use for processing a powder, which is a composition of iron particles, pigment and lacquer which is introduced in a solid form onto the surface of the workpiece. The solvent acts as the fixing medium, which cause the particles of the powder which the lacquer is at least partially softened to adhere to each other and to the surface of the workpiece. Such a powder and a process for its introduction are described in the Swiss Patent Application Nos. 16404/74 and 6311/75.

Figure 20:
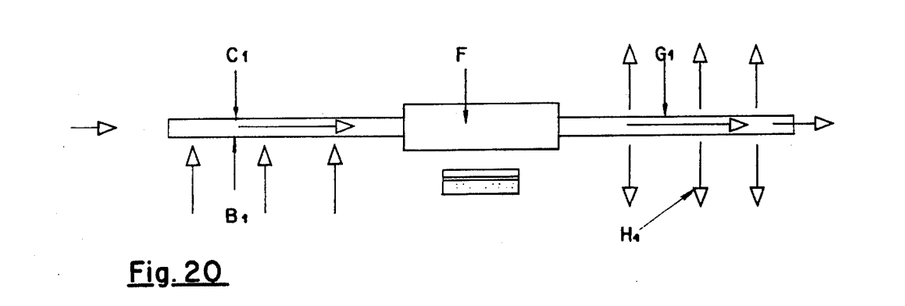
FIGS. 20–22 the installation with various variations of the feed unit and the unit for carrying of workpieces, in outline.
Figure 21:
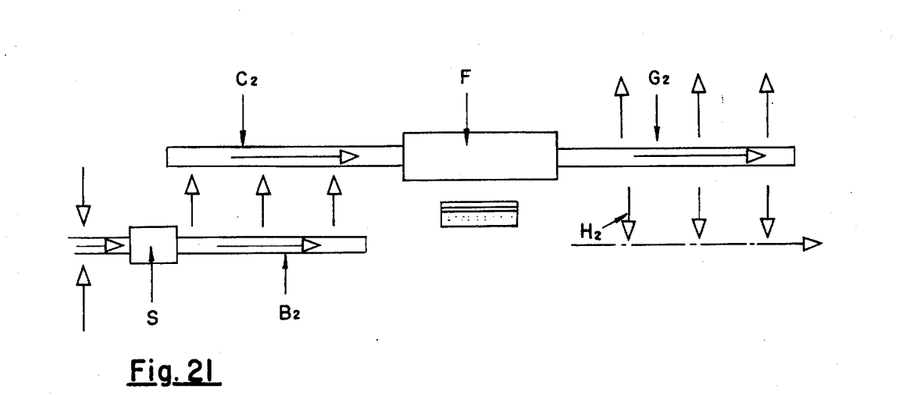
Figure 22:
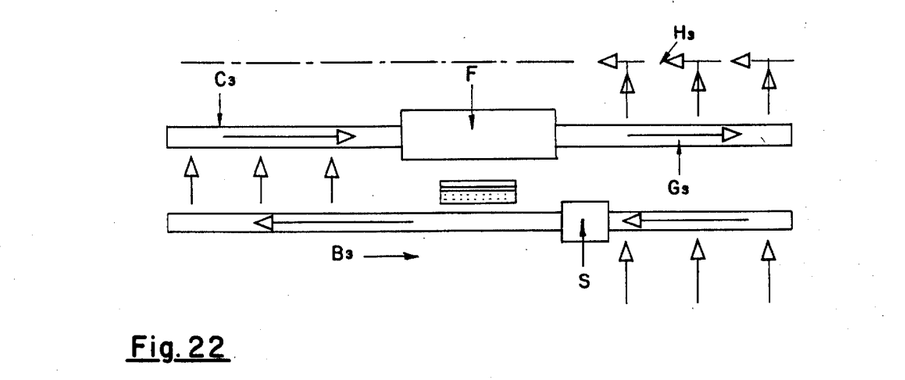

FIGS. 20-22 show various embodiments of the feed unit and the carrying off unit. According to FIG. 20 the feed unit $B_1$ can supply the workpieces which are to be treated either transversely or in the direction of travel to the feed station $C_1$. At the delivery station $G_1$ the workpieces which have been treated can either be transported away by means of the carrying off device $H_1$ either in the direction of feed or transversly to it to one or the other side.

In the embodiment shown in FIG. 21 the feed unit $B_2$ has a cleaning device S in which the workpiece to be treated are first of all cleaned, particularly from scale and rust, before they are supplied to the feed station $C_2$. The carrying-off device $H_2$ corresponds to that shown in FIG. 20.

The installation according to FIG. 22 also has a cleaning device S in the feed unit $B_3$ in which the workpiece which are to be treated are first of all freed of dirt, rust and scale, before they are fed to the feed station $C_3$. At the delivery station $G_3$ the workpieces are removed obliquely to the direction of supply and are carried away in the carrying-off device $H_3$ opposite to the direction of supply to the delivery station.

Figure 23:
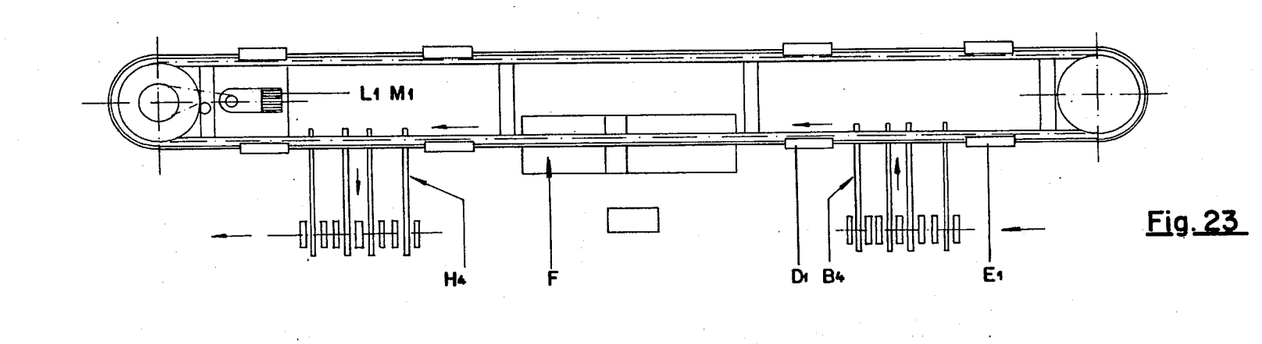
FIG. 23 a further installation for showing up faulty areas on the surface of bar-shaped magnetizable workpieces with clamping devices which are guided in a closed path, in outline.
Figure 24:
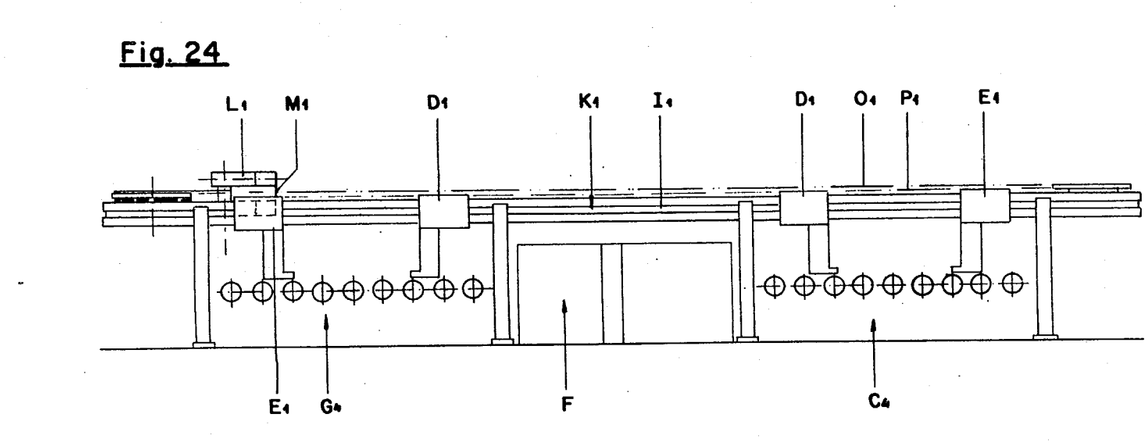
FIG. 24 a side-view of the installation in FIG. 23.
Figure 25:
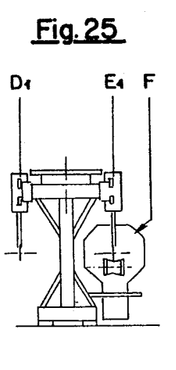
FIG. 25 an end-view of the installation of FIG. 24.

FIGS. 23-25 show a further embodiment of the installation, in which the support $K_1$ and the guide rails $I_1$ are arranged to form an endless track. The installation contains at least two, preferably four, pairs of clamping devices $D_1,E_1$, which also in this case are movable by means of drive cables $O_1,P_1$ and device $L_1,M_1$. The spacing of the clamping devices $D_1,E_1$ which are arranged in pairs are preferably of equal size and so arranged, that in each case at the same time one pair of the clamping device $D_1,E_1$ is at the feed station $C_4$ and one pair is at the delivery station $G_4$. With this arrangement of the installation it is possible to provide for, that immediately when a workpiece is released at the delivery station $G_4$, without return motion of the clamping devices $D_1,E_1$, a new workpiece can be taken up immediately at the feed station $B_4$. Should the workpieces which are to be handled always have the same length, the installation according to FIGS. 23-25 can not only be equipped with one feed station $C_4$, one treatment station $F_1$ and one delivery station $G_4$, bur rather as a mirror image of this on the back have a second feed station, a second treatment station and a second delivery station with corresponding feed units and carrying-off units. By means of such an embodiment, which is not shown, the performance of such an installation can be doubled.

The present installation for showing up faulty areas on the surface of bar-shaped magnetizable workpiece is distinguished overally by outstanding recognition of faulty areas, high efficiency, and low need for maintenance and proneness to breakdown.

We claim:

1. An installation for detecting and marking defective locations in the surface of an elongated rigid workpiece of magnetizable material, comprising at least one pair of clamping devices for engaging the ends of the workpiece and to clamp the workpiece in its longitudinal direction, means for connecting said clamping devices to an electric current source for passing a current through the workpiece so as to create magnetic flux lines of a magnetic field at the surface of the workpiece, guide rail means providing a track for at least one pair of first and second carriages movable along said track and each carrying one of said clamping devices, said guide rail means and carriages serving for conveying the workpiece from a feed station to a delivery station while current is passing through the workpiece, a treatment station arranged between said feed station and said delivery station, so that the work piece travels through the treatment station when it is conveyed from the feed station to the delivery station, said treatment station having a spraying device for spraying a ferromagnetic powder on the surface of the workpiece, and a fixing device for fixing the powder which magnetically adheres to defective locations in said surface, said first and second carriages being associated with a first and a second drive cable, respectively, each having two opposite ends which both are connected to the associated carriage, said drive cables being parallel and each running along said guide rail means and over two return pulleys arranged beyond the feed station and the delivery station, respectively, so that the first and second drive cables each form a closed loop, two drive devices operatively connected to said first and second drive cables, respectively, for moving the corresponding first and second carriages along said track, a clutch coupling for connecting together and disconnecting the two drive devices, for selectively allowing joint or independent movement of the carriages, respectively.

2. An installation as claimed in claim 1, wherein said first and second carriages support first and second tension devices, respectively, for maintaining pretensioned the associated first and second drive cables, each said tension device comprising a spring means interconnected between one end of the associated first and second drive cables and the corresponding carriage, the other end of the first drive cable being adjustably fastened to said first carriage, while the other end of the second drive cable is adjustably connected to a sliding member which is slidably supported by said second carriage, a supplementary tension device having a spring means being interconnected between said sliding member and said second carriage, said sliding member and supplementary tension device being arranged so that the sliding member is displaceable with respect to the second carriage against the action of the spring means of the supplementary tension device when said workpiece is engaged by said pair of clamping devices upon independent movement of said first and second carriages one toward the other.

3. An installation as claimed in claim 2, wherein said sliding member comprises a cylindrical portion which is surrounded by said spring means of the supplementary tension device, said spring means being constituted by a compression spring with two opposite ends, one of which abuts against an end plate of said cylindrical portion and the other one abuts against a fixed portion of said second carriage, said first and second tension devices being arranged within a cylindrical housing fixed on said first carriage and within said cylindrical portion of said sliding member, respectively.

4. An installation as claimed in claim 3, wherein the spring means of each said first and second tension devices is constituted by a compression spring with two opposite ends, one of which abuts against an end plate of said cylindrical housing and said cylindrical portion of the sliding member respectively, the other end of the spring abutting against a piston which is slidably guided in said cylindrical housing and said cylindrical portion of the sliding member respectively, and which is connected to said other end of the first and second drive cables, respectively.

5. An installation as claimed in claim 4, wherein said cylindrical portion of the sliding member and said cylindrical housing are provided with longitudinal slots which are in engagement with projections fixedly arranged at the second carriage and at the piston in the cylindrical housing, respectively, for preventing said cylindrical portion and housing from rotation, the ends of said drive cables being each secured to threaded sleeves which in turn are fastened to a fixed portion of the first carriage, to a portion of the sliding member and to one and the other of said pistons, respectively, by means of nuts and check nuts, and means being provided for preventing twisting of said drive cables.

6. An installation as claimed in claim 2, wherein an auxiliary drive device and an auxiliary clutch coupling are provided, said auxiliary drive device being connectable, by means of said auxiliary clutch coupling, to one of said drive devices when said clutch coupling between said two drive devices is disengaged, in order to move one of said carriages with respect to the other at a reduced speed.

7. An installation as claimed in claim 6, wherein said second carriage has a monitoring device which is operatively connected to said sliding member so as to monitor loading of the spring means of said supplementary tension device when said workpiece is engaged by said pair of clamping devices.

8. An installation as claimed in claim 7, wherein said sliding member is connected to a control bar extending substantially in a direction parallel to said guide rail means and having a first cam part for indicating inadequate loading and a second cam part for indicating adequate loading of the spring means of said supplementary tension device, a cam follower associated with said control bar, said cam follower being arranged on said second carriage for movement substantially in a direction at right angles with respect to said guide rail means, and means being provided for transmitting movement of said cam follower to an electric switch means for controlling operation of said auxiliary drive device.

9. An installation as claimed in claim 8, wherein said electric switch means comprises a plurality of switches which are arranged at said guide rail means and spaced apart from each other along said guide rail means, said cam follower carrying an elongated actuating rail extending parallel to said guide rail means, said actuating rail having a length greater than the spacing of said switches and being arranged to actuate at least one of said switches, independently of the actual position of said second carriage along said guide rail means.

10. An installation as claimed in claim 6, wherein said drive devices each have a motor with a gear unit, said clutch device being arranged between the gear units of said drive devices, and said auxiliary clutch device being arranged between the auxiliary drive device and the motor of said one drive device.

11. An installation as claimed in claim 1, wherein said guide rail means form a straight track along which said carriages are movable in alternating directions.

12. An installation as claimed in claim 1, wherein said guide rail means form an endless track along which said carriages are movable in continuous direction, at least two pairs of carriages with associated clamping devices being provided and arranged so that one pair of the clamping devices is located at said feed station while another pair of the clamping devices is disposed at said delivery station.

* * * * *